US00PP36299P2

(12) United States Plant Patent
Bachès

(10) Patent No.: US PP36,299 P2
(45) Date of Patent: Dec. 10, 2024

(54) LEMON TREE NAMED 'PLBA1'

(50) Latin Name: *Citrus limon*
Varietal Denomination: PLBA1

(71) Applicant: BioGold Network EM S.A., Seville (ES)

(72) Inventor: Michel Bachès, Eus (FR)

( * ) Notice: Subject to any disclaimer, the term of this patent is extended or adjusted under 35 U.S.C. 154(b) by 0 days.

(21) Appl. No.: 18/435,352

(22) Filed: Feb. 7, 2024

(51) Int. Cl.
*A01H 5/08* (2018.01)
*A01H 6/78* (2018.01)

(52) U.S. Cl.
USPC ..... Plt./201
CPC ..... *A01H 6/785* (2018.05)

(58) Field of Classification Search
USPC ..... Plt./156, 201
See application file for complete search history.

(56) References Cited

PUBLICATIONS

CPVO Application Consultation. 2020. citation for PLBA1. https://online.plantvarieties.eu/publicConsultationDetails?registerId=20201166&denomination=PLBA1. 2 pages (Year: 2020).*

* cited by examiner

*Primary Examiner* — Karen M Redden
(74) *Attorney, Agent, or Firm* — Michelle Bos Legal LLC

(57) ABSTRACT

A new lemon tree named 'PLBA1', which originated as a spontaneous mutation of 'Eureka' lemon and is distinguished by its light yellowish-pink-fleshed fruit.

5 Drawing Sheets

Latin name: *Citrus limon.*
Variety denomination: 'PLBA1'.

BACKGROUND AND SUMMARY OF THE VARIETY

'PLBA1' is a new lemon tree that originated as a spontaneous mutation of a 'Eureka' lemon tree (not patented). The mutation was discovered in a cultivated 'Eureka' orchard at Eus, Pyrénées-Orientales, France in 2005, when fruit was observed by the inventor to have light, yellowish-pink pigmented flesh. The 'PLBA1' lemon tree was first propagated by grafting at Eus in 2005, and has been found to exhibit its distinctive characteristics and remain stable through successive asexually propagated generations.

The seeded yellowish-pink-fleshed fruit of the 'PLBA1' lemon tree is easily distinguished from the seeded yellow-fleshed fruit of parent tree 'Eureka', and from the seedless yellow-fleshed fruit of similar lemon tree variety '7ELS1' (U.S. Plant Pat. No. 24,608).

BRIEF DESCRIPTION OF THE PHOTOGRAPHS

The accompanying photographs, taken in 2021 at Visalia, California, show 2-year-old trees grown on *Citrus macrophylla* rootstock (not patented).

Figure 1:
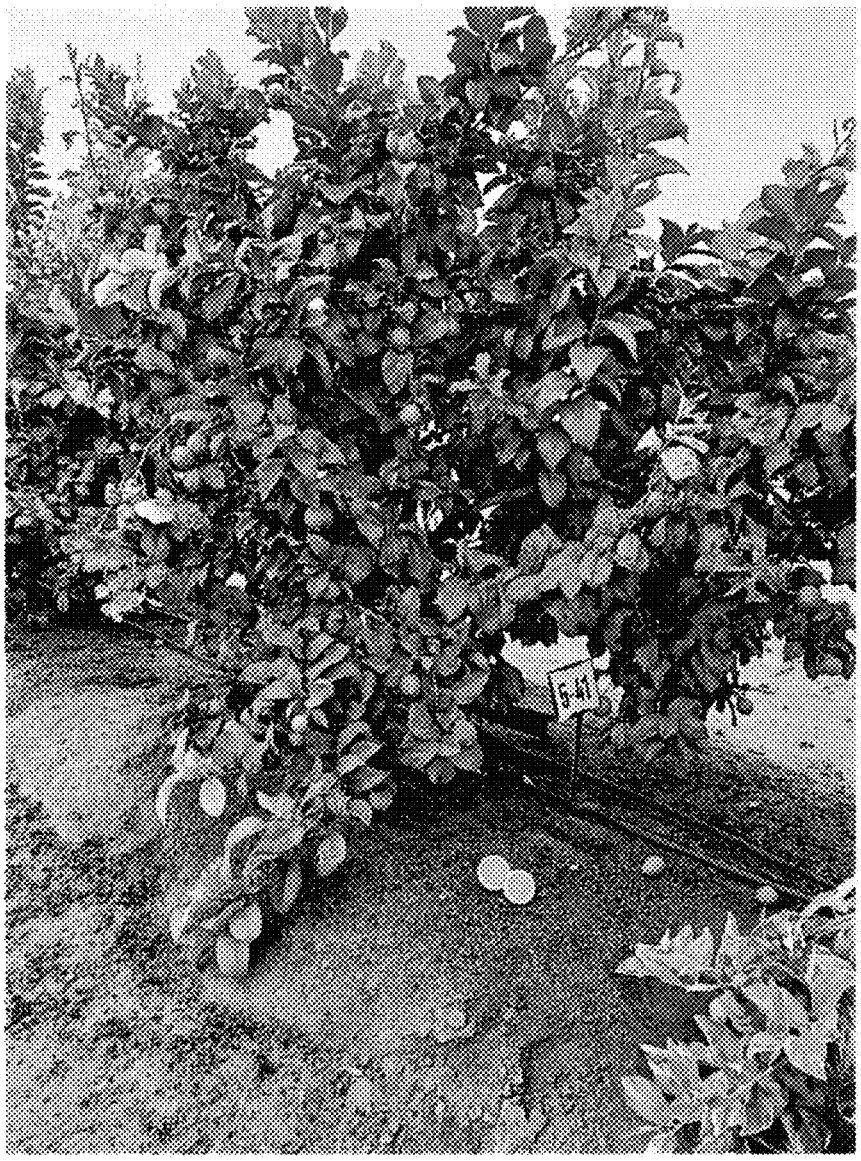
FIG. 1 shows a 'PLBA1' lemon tree.
Figure 2:
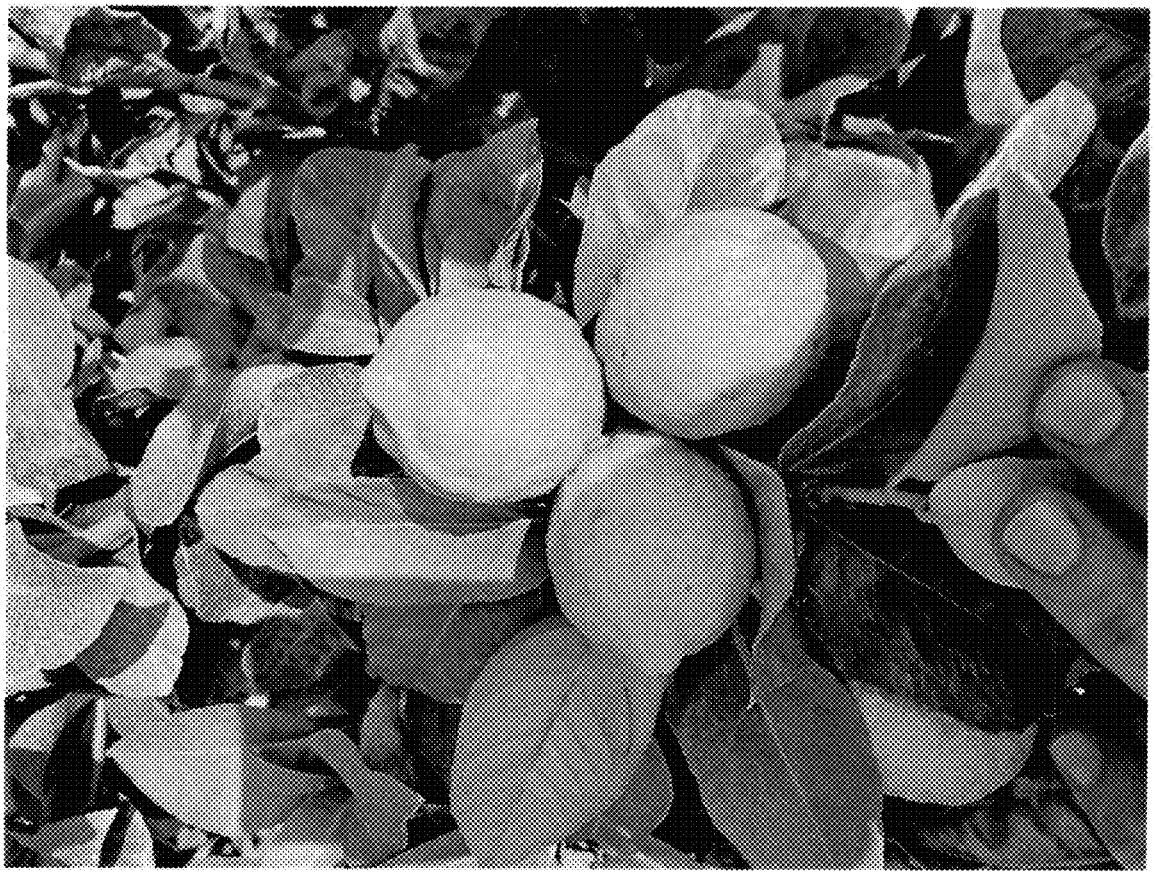
FIG. 2 shows whole fruit and leaves of a 'PLBA1' lemon tree.
Figure 3:
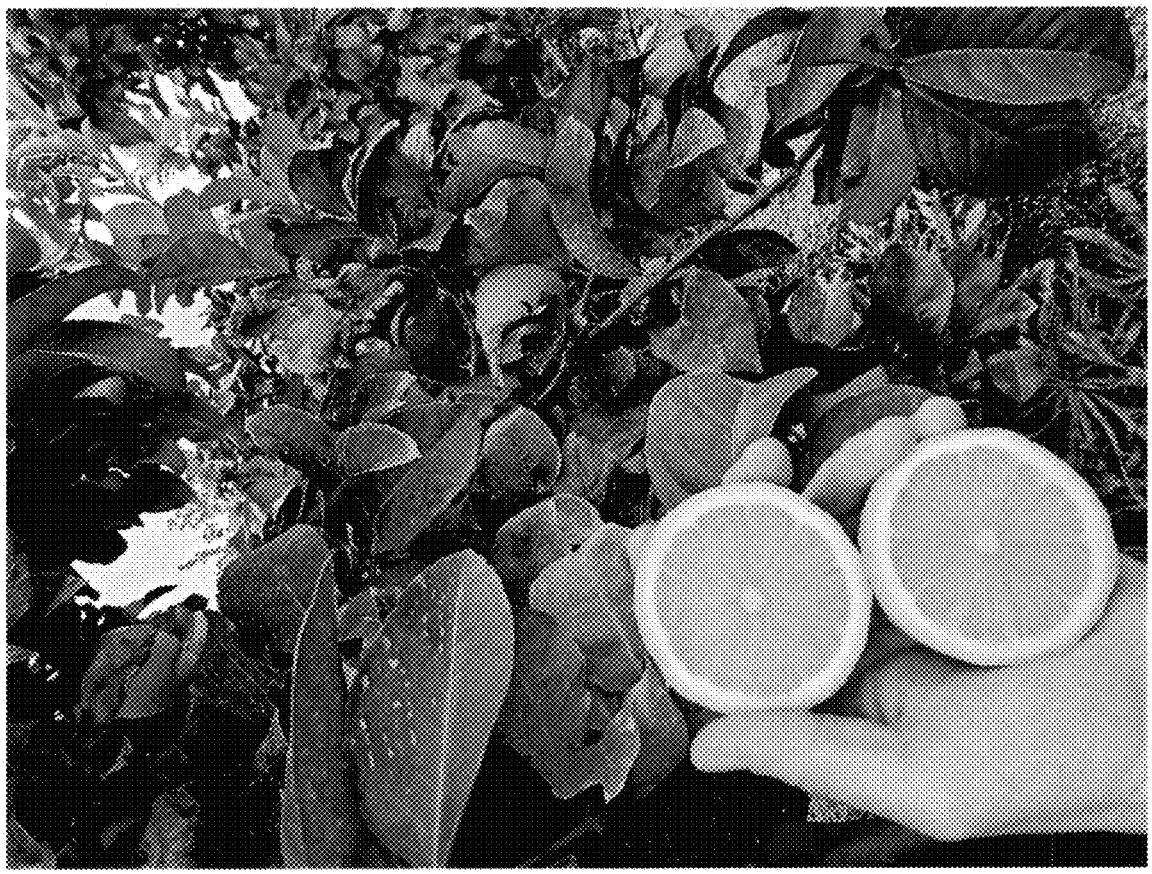
FIG. 3 shows a sectioned fruit and leaves of a 'PLBA1' lemon tree.
Figure 4:
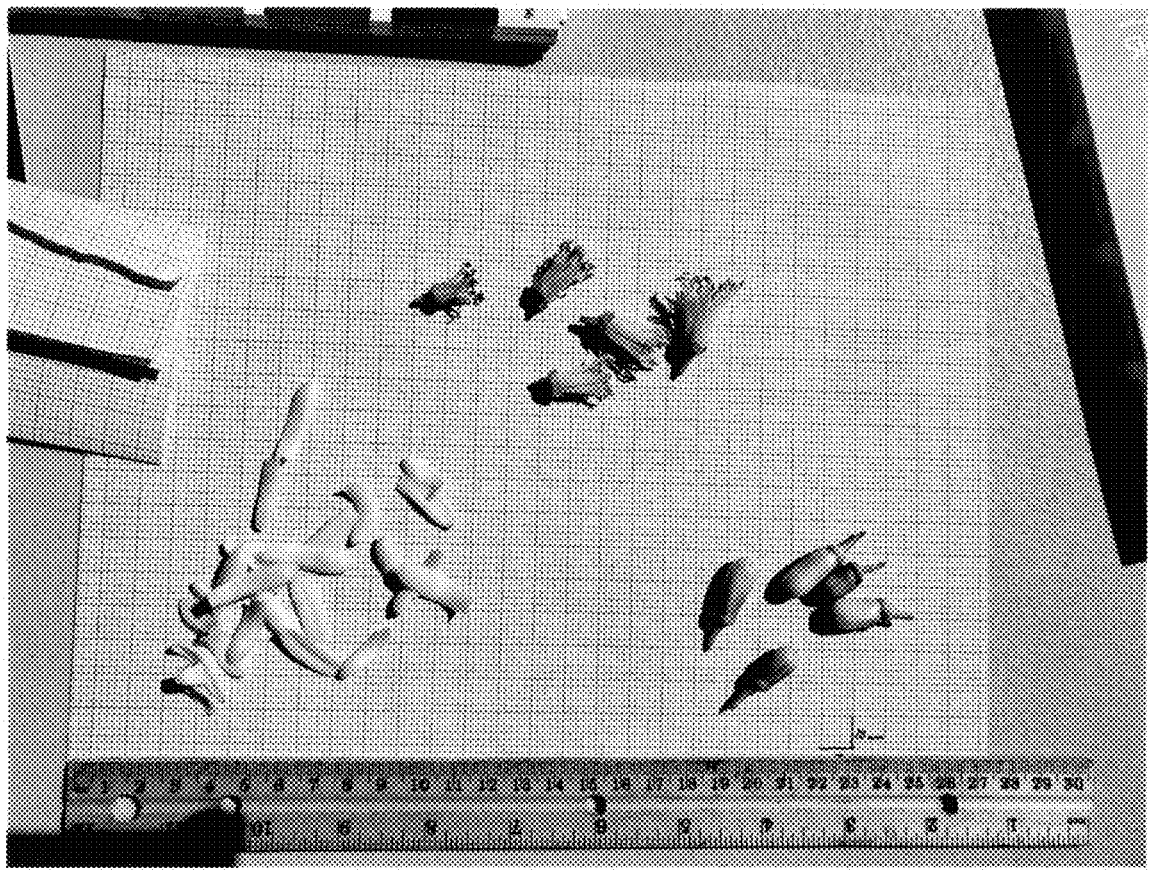
FIG. 4 shows dissected blossoms from a 'PLBA1' lemon tree.
Figure 5:
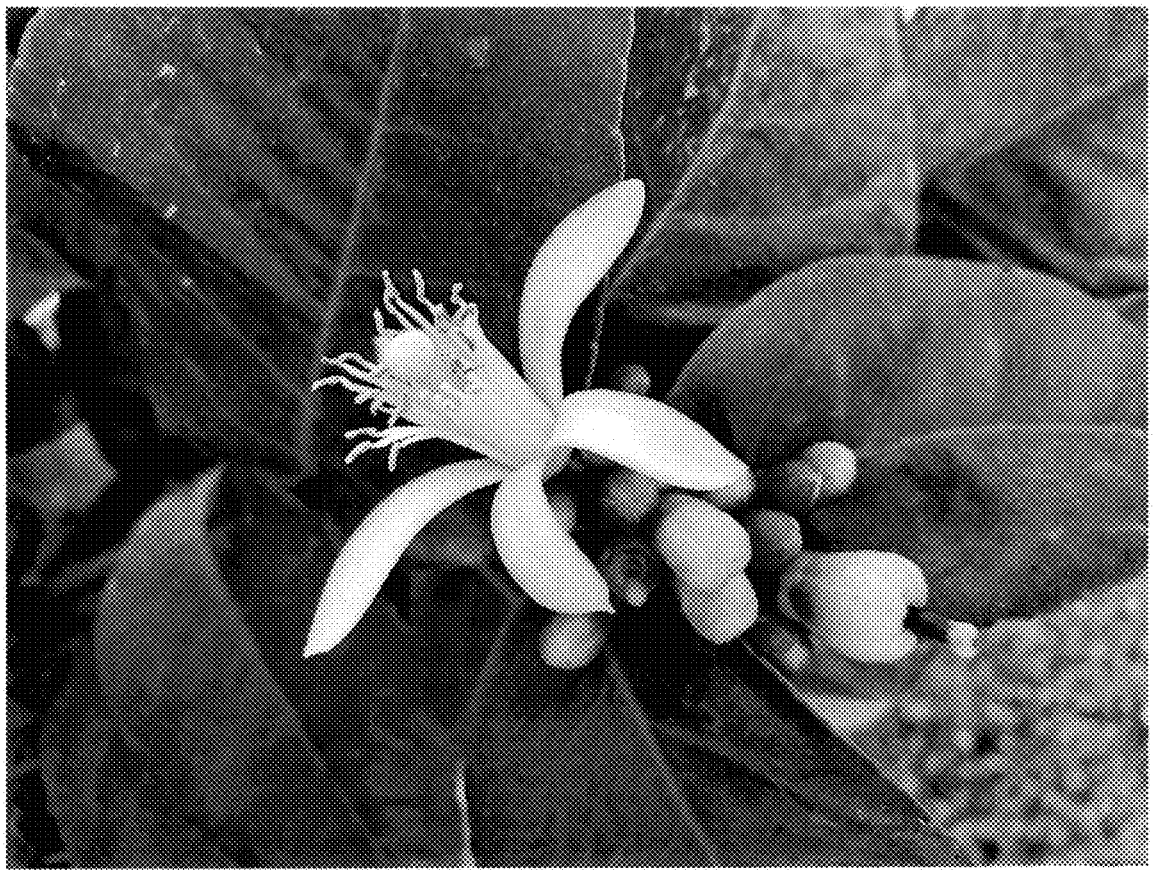
FIG. 5 shows a blossom on a 'PLBA1' lemon tree.

Because lighting conditions can affect the colors shown in photographic illustrations, color characteristics of the claimed variety should be determined with reference to the observations described herein, rather than from the illustrations alone.

DETAILED BOTANICAL DESCRIPTION

The following detailed botanical description is based on observations recorded in 2021 at Visalia, California, of 2-year-old trees grown on *Citrus macrophylla* rootstock. The characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Colors are described with reference to The R.H.S. Colour Chart (Royal Horticultural Society, $6^{th}$ ed.).

Tree:
- *Vigor.*—Medium.
- *Density of canopy.*—Medium.
- *Habit.*—Spreading.
- *Height.*—2.4 m.
- *Spread.*—1.8 m.
- *Trunk diameter* (*at* 30 *cm above graft*).—4.3 cm.
- *Bark texture.*—Smooth.
- *Bark color.*—Grey-brown 199D.
- *Tendency toward alternate bearing.*—None.
- *Chilling requirement.*—None.

Branch (fruiting branch located about 1 m above graft union):
- *Length.*—120 cm.
- *Diameter.*—2.8 cm.
- *Crotch angle.*—Medium.
- *Bark color.*—Older growth grey-brown 199B with green 143A.

*Bark texture*.—Smooth.
*Thorns*.—Few.
*Thorn length*.—1.8 cm.
*Current year shoot length*.—91 cm to 97 cm.
*Current year shoot color*.—Yellow-green 144A.

Flowers:
*Bud shape*.—Oblong.
*Bud length*.—16 mm.
*Bud diameter*.—8 mm.
*Bud color*.—Green-white 157A with red-purple 64B at base.
*Quantity of blossoms per cluster*.—3 to 10.
*Blossom diameter*.—35 mm.
*Blossom depth*.—22 mm.
*Pollen color*.—Yellow 7A.
*Sepal length*.—6 mm.
*Sepal width*.—4 mm.
*Sepal shape*.—Fused, acuminate tip.
*Sepal margin*.—Entire.
*Sepal color-upper surface*.—Yellow-green 145C with red-purple 64B tips.
*Sepal color-lower surface*.—Yellow-green 145C.
*Quantity of petals per flower*.—5.
*Petal shape*.—Oblong.
*Petal apex*.—Mucronate.
*Petal margin*.—Entire.
*Relative position of petal margins*.—Separate, not overlapping.
*Petal length*.—21 mm.
*Petal width*.—7 mm.
*Petal color-upper surface*.—White N155A.
*Petal color-lower surface*.—White N155A with some red hue.
*Bloom date*.—Multiple; main bloom is March and April.
*Date of first fruitlet fall*.—Drop from main bloom occurs in May.
*Pedicel length*.—7 mm.
*Pedicel diameter*.—3 mm.
*Pedicel color*.—Yellow-green 145C.
*Pistil quantity per flower*.—1.
*Pistil length*.—15 mm.
*Pistil color*.—Yellow 10C to yellow 10D.
*Anther quantity per flower*.—25 to 30.
*Anther length*.—2.4 mm.
*Anther color*.—Yellow-orange 14C.
*Stigma length*.—2 mm to 3 mm.
*Stigma color*.—Yellow 10C.
*Style length*.—8 mm.
*Style color*.—Yellow 10D.
*Ovary length*.—5 mm.
*Ovary diameter*.—3 mm.
*Ovary color*.—Yellow-green 144C.

Leaves:
*Length*.—11.4 cm.
*Width*.—5.9 cm.
*Length/width ratio*.—1.9:1.
*Blade margin*.—Entire, slightly crenate.
*Leaf shape*.—Lanceolate.
*Apex shape*.—Acute.
*Base shape*.—Aequilateral to cuneate.
*Color of upper surface*.—Green NN137A.
*Color of lower surface*.—Green 143B.
*Leaf texture* (*upper surface*).—Glabrous.
*Petiole length*.—10 mm.
*Petiole diameter*.—2.3 mm.
*Petiole color*.—Yellow-green N144A.
*Wings*.—None.

Fruit:
*Quantity per cluster*.—1 to 3.
*Axial diameter*.—6.4 cm.
*Apical diameter*.—8.3 cm.
*Weight*.—154 g.
*General shape in profile*.—Ellipsoid.
*Navel*.—None.
*Rind color*.—Yellow 9A.
*Rind color pattern*.—Solid.
*Oil glands per cm*$^2$.—About 35.
*Oil gland diameter*.—0.5 mm.
*Rind thickness*.—5 mm including albedo.
*Rind texture*.—Puncticulate.
*Albedo thickness*.—2 mm to 3 mm.
*Quantity of fruit segments per fruit*.—9 to 10.
*Juice sac length*.—1.6 mm.
*Juice sac shape*.—Variable, mostly elongate.
*Juice sac length to width ratio*.—1.6:1.
*Juice sac color*.—Red 36A (light yellowish pink).
*Juice soluble solids* (° *brix*).—6.0 to 6.5.
*Harvest window*.—Multiple sets; Main crop is November through February.
*Quantity of seeds per fruit*.—0 to 3.
*Seed length*.—8.5 mm.
*Seed diameter*.—5 mm.
*Seed color*.—Greyed-yellow 160C.
*Stem length*.—20 mm.
*Stem diameter*.—5 mm.
*Stem color*.—Yellow-green N144C.

Diseases and pests: No distinguishing resistance or susceptibility noted.
Market use: Fresh.
Keeping quality: Good.

The invention claimed is:

1. A new and distinct lemon tree named 'PLBA1' substantially as illustrated and described herein.

* * * * *